(12) United States Patent
Sunkel et al.

(10) Patent No.: US 7,064,140 B2
(45) Date of Patent: Jun. 20, 2006

(54) SYNERGISTIC COMBINATIONS INCLUDING N-ACYLATED 4-HYDROXYPHENYLAMINE DERIVATIVES AND CAFFEINE

(76) Inventors: Carlos Sunkel, Calle Almarza #47, 28033, Madrid (ES); Nicolas G. Bazan, LSUHSC, 2020 Gravier St., New Orleans, LA (US) 70112; Dennis Paul, Dept. of Pharmacology, 1901 Perdido St., New Orleans, LA (US) 70112; Julio Alvarez-Builla, Universidad de Alcala de Henares Depto. de Quimica Organiza Campus Universitario Facultad de Farmacia Carretera Madrid-Barcelona, Km 33,600, 28871 Alcala de Henares, Madrid (ES)

(*) Notice: Subject to any disclaimer, the term of this patent is extended or adjusted under 35 U.S.C. 154(b) by 0 days.

(21) Appl. No.: 10/459,911

(22) Filed: Jun. 12, 2003

(65) Prior Publication Data

US 2004/0254207 A1    Dec. 16, 2004

Related U.S. Application Data

(63) Continuation-in-part of application No. 10/292,105, filed on Nov. 12, 2002, now Pat. No. 6,864,271.

(51) Int. Cl.
*A61K 31/425* (2006.01)
(52) U.S. Cl. ...................................................... 514/373
(58) Field of Classification Search ................. 514/373
See application file for complete search history.

(56) References Cited

U.S. PATENT DOCUMENTS 5,554,636 A * 9/1996 Bazan et al. ................. 514/373
5,621,110 A * 4/1997 Bazan et al. ................. 548/210

* cited by examiner

*Primary Examiner*—Taofiq Solola
(74) *Attorney, Agent, or Firm*—Adams and Reese LLP

(57) ABSTRACT

The present invention relates to pharmaceutical combinations of opioid and non-opioid analgesics in an intimate admixture with caffeine and an analgesic from a series of N-acylated 4-hydroxyphenylamine derivatives, linked via an alkylene bridge to the nitrogen atom of a 1,2-benzisothiazol-3(2H)-one 1,1-dioxide group and methods for their use to alleviate pain in mammals. The analgesic combinations exhibit enhanced analgesic potency and are free from antipyretic activity, do not suppress blood coagulation, and have little hepatotoxic effect.

36 Claims, No Drawings

SYNERGISTIC COMBINATIONS INCLUDING N-ACYLATED 4-HYDROXYPHENYLAMINE DERIVATIVES AND CAFFEINE

CROSS REFERENCE TO RELATED APPLICATIONS

This is a continuation-in-part of U.S. patent application Ser. No. 10/292,105, filed on Nov. 12, 2002 now U.S. Pat. No. 6,846,271, the disclosure of which is herein incorporated by reference.

STATEMENT REGARDING FEDERALLY SPONSORED RESEARCH OR DEVELOPMENT

Not applicable

REFERENCE TO A MICROFICHE APPENDIX

Not applicable

COPYRIGHT NOTICE

Not applicable

FIELD OF THE INVENTION

The present invention relates to analgesic compositions that are free from antipyretic activity, do not suppress blood coagulation, have little hepatotoxic effect. The analgesic compositions include caffeine for enhancing the analgesic activity of the N-acylated 4-Hydroxyphenylamine derivatives disclosed herein, as well as enhancing the efficacy and/or potency of certain opioid and non-opioid analgesics. More particularly, the present invention relates to analgesic compositions that include analgesics referred to as the SCP series (SCP-1 through SCP-5) in combination with caffeine and additional opioid and non-opioid analgesics.

BACKGROUND OF THE INVENTION

Caffeine is a naturally occurring methylxanthine (1,3,7-trimethylxanthine) derived from several plants, including coffee, cocoa and cola. It is classified as a mild central nervous system stimulant. It is commonly used to combat fatigue and has some benefit in the treatment of migraine headaches. By itself it has little or no analgesic efficacy, but caffeine will enhance the action of analgesic drugs by 10–40%, particularly acetaminophen and opioids.

The methylxanthines exhibit complex mechanistic and pharmacological pathways affecting a variety of signaling pathways. With regard to nociception, the two most important mechanisms of action are their ability to block receptor-mediated actions of adenosine and their ability to inhibit cyclic nucleotide phosphodiesterase enzymes.

Adenosine is a nearly ubiquitous inhibitory neuromodulator. Importantly, it plays a key role in the production of sleep. Therefore, the blockade of adenosine receptors by methylxanthines will cause alertness. Research has shown that adenosine modulates the release of the neurotransmitter, norepinephrine. Norepinephrine is an important neurotransmitter in the descending inhibitory circuitry activated by dihydromorphine and other mu opioid receptor agonists. Therefore it follows that the blockade of adenosine receptors by methylxanthines also modulates the activity of opioid analgesics.

With regard to the inhibition of phosphodiesterase enzymes, which catalyzes the breakdown of cyclic AMP to 5'-AMP and cyclic GMP to 5'-GMP, the presence of methylxanthines will cause accumulation of the two cyclic nucleotides, resulting in an increase in the signal transduction mediated by these pathways. Thus, caffeine modulates the signaling initiated by many of the G-protein coupled receptors, including opioid receptors.

Compositions containing NSAIDs (non-steroidal anti-inflammatory drugs) in combination with varying amounts of caffeine have been marketed in the past. Examples include combinations containing aspirin, acetaminophen, and/or phenacetin. Narcotic analgesics have also been added to the aspirin/acetaminophen/phenacetin/caffeine combinations. The rational for using such combinations is to reduce the dose of each analgesic, and thus reduce adverse effects and toxicity, while retaining or increasing analgesic efficacy.

For many types of pain (e.g. common headache, osteoarthritis) acetaminophen has equal potency and efficacy to acetylsalicylic acid (aspirin). However, the safety of acetaminophen has been questioned. There are approximately 100,000 cases of acetaminophen overdose annually, with approximately 30 deaths resulting. (Clissold, 1980; McGoldrick et al. 1997). Acetaminophen has a toxic metabolite, N-acetyl-benzoquinoneimine (NAPQI), which depletes hepatic and renal glutathione, a cytoprotective endogenous metabolite (Mason & Fischer, 1986; Mitchell et al., 1983). Hepatic and renal toxicity with acetaminophen can occur at doses only 4- to 8-fold higher than the maximum recommended analgesic dose (Neuberger et al., 1980). Pharmaceutical combinations that contain acetaminophen and a centrally acting analgesic may be even more dangerous than acetaminophen alone. With repeated use these combinations require higher doses to produce the same analgesic effect because of an increase in tolerance. As the dose of the combination is increased to compensate for analgesic tolerance, the safety of the drug decreases as the higher doses of the acetaminophen component increase hepatic and renal toxicity.

In U.S. Pat. No. 5,554,636 (Bazan et al.) and U.S. Pat. No. 5,621,110 (Bazan et al.), two of the inventors herein disclosed the series of N-acylated 4-hydroxyphenylamine derivatives linked via an alkylene bridge to the nitrogen atom of a 1,2-benzisothiazol-3(2H)-one 1,1-dioxide group along with the process for their preparation and methods of their use for alleviating pain. The disclosures of these patents are incorporated herein by reference. The SCP series is structurally depicted by the following general formula:

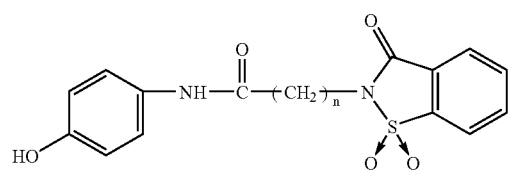

wherein n is a number from 1 to 5. These new non-narcotic analgesics surprisingly possess high analgesic activity free from antipyretic activity, do not suppress blood coagulation, and display little hepatotoxic effect. When the term "SCP series" is used herein, it is understood that any of the pharmaceutically suitable salts thereof are included by the term.

The analgesic profiles of the SCP series are at least as good as that of acetaminophen. As expected, both types of drugs show little or no activity in the tail-flick and hotplate tests when compared with codeine. SCP-1 is more potent in the abdominal stretch, formalin, and Freund's adjuvant-induced inflammation assays of analgesia than acetaminophen. Acetaminophen is a potent antipyretic, whereas SCP-1 at doses up to 904 µmoles/kg (300 mg/kg) has no antipyretic effect. SCP-1 is lower in toxicity, and, of even greater importance, lower in hepatotoxicity (Paul et al., 1998). All of these properties make SCP-1 and related derivatives potentially very useful pharmacologic agents.

These novel non-narcotic analgesics differ substantially in chemical structure from aspirin, acetaminophen and phenacetin and have significantly different biological profiles, thus the SCP series of analgesics can be formulated into novel pharmaceutical combinations with caffeine to elicit enhanced analgesia without antipyretic activity and little hepatotoxic effect.

DESCRIPTION OF THE PREFERRED EMBODIMENTS

The most commonly employed method of managing pain involves the systemic administration of analgesics. Analgesics by definition include drugs that through their action on the nervous system reduce or abolish the perception of pain without producing unconsciousness. Traditionally, analgesics fall into two broad categories: (1) simple, non-narcotic analgesics, such as aspirin, which appear to work by inhibition of prostaglandin synthetase, and (2) narcotic analgesics, which appear to work through interaction with the endorphin/enkephalin receptor system of the central nervous system. The term "narcotic" has historically been associated with the strong opioid analgesics, but the term is not very useful in a pharmacological context. More appropriately, the category referred to as narcotic analgesics, can be further divided into two groups, the opioids and non-opioids. The term "opioids" refers to drugs with morphine like activity (agonists and antagonists), acting on mu, delta and kappa receptors. The term "non-opioids" refers to drugs that act via a different mechanism.

The drugs that comprise the group known as the opioid analgesics include among others the phenanthrene alkaloids of opium, comprising morphine, codeine, and thebaine. While thebaine produces no analgesia, it is an important intermediate in the production of semisynthetic opioids. Other agents with structures and function related to morphine include: (1) the morphine analogs, such as hydromorphone, oxymorphone, hydrocodone, and oxycodone; (2) Diels-Alder adducts, such as etorphine and buprenorphine; (3) the morphinan derivatives, such as dextromethorphan and butorphanol; (4) the benzomorphan derivatives, such as phenazocine, pentazocine and cyclazocine; (5) the piperidine derivatives, such as meperidine and anileridine; and (6) open chain analgesics (methadone type compounds), such as methadone and propoxyphene. The drugs that comprise the group known as the non-opioid analgesics include: (1) N-methyl-D-aspartate (NMDA) receptor antagonists, such as dextromethorphan and ketamine and other antagonists that suppress central sensitization by competing for any of the binding site subcategories associated with the NMDA receptor, e.g., the glycine binding site, the phenylcyclidine (PCP) binding site, etc., as well as the NMDA channel; (2) alpha$_2$ adrenoreceptor agonists, such as clonidine, metomidine, detomidine, dexmetomidine, dexmedetomidine and xylazine, that reduce the release of norepinephrine; (3) other agents, such as tramadol, often mistakenly referred to as an opioid, that produce analgesia by their inhibitory actions on monoamine re-uptake rather than by agonist effect; (4) non-steroidal anti-inflammatory drugs such as aspirin, ibuprofen and other drugs that inhibit cyclooxygenase enzymes and (5) mixed agonist-antagonist analgesics such as buprenorphine, dezocine, nalbuphine.

Opioid and non-opioid analgesics may cause a variety of side effects including sedation, constipation, hypotension, nausea, vomiting, elevation of cerebrospinal fluid pressure, respiratory depression, physical dependence and tolerance. Therefore, there is a serious need to develop combinations of drugs that supplement the activity of the opioid and non-opioid analgesics, which allows the use of smaller doses of the opioid and non-opioid analgesics. One way of achieving this result is to enhance the analgesic activity of a known opioid or non-opioid analgesic by the addition of a second non-narcotic analgesic. However, it is difficult to predict when a synergistic effect will be obtained from two pharmaceutical compositions that take effect through different mechanisms.

The SCP series are non-narcotic analgesics that are free from antipyretic activity and have little hepatotoxic effect. The compounds in this series do not produce the metabolite that is responsible for acetaminophen toxicity and they do not reduce fever. As a result, they are more useful than acetaminophen and other non-narcotic analgesics in the treatment of chronic pain and in situations in which controlling fever is contraindicated, such as after surgery, where fever control can mask infection. Moreover, unlike conventional non-narcotic analgesics, such as aspirin or ibuprofen, the SCP series does not suppress blood coagulation. Children, the elderly and liver-compromised patients would also benefit from the administration of SCP for the treatment of pain. Pharmaceutical combinations utilizing the SCP series with opioid and non-opioid analgesics has been found to provide enhanced analgesia without antipyretic activity, without suppressing blood coagulation, and without the toxicity associated with conventional non-narcotic analgesics.

Caffeine has a long history for use in the treatment of headaches. The term "caffeine" as used herein is intended to encompass not only caffeine as the anhydrous powder, but any salt or derivative of caffeine or any compounded mixture thereof, which is nontoxic and pharmaceutically acceptable. By itself, caffeine has little or no analgesic effect. However, caffeine will enhance, or potentiate, the analgesic activity of acetaminophen. In human trials, only a dose greater than 50 mg of caffeine will significantly potentiate acetaminophen or NSAID analgesia (Laska et al., 1984; Zhang 2001; Zhang & Po, 1997). Caffeine potentiation of acetaminophen analgesia is likely due to a change in the pharmacokinetics of acetaminophen (Granados-Soto et al., 1993).

It has also been shown that caffeine will potentiate the analgesic effect of opioid analgesics. Although most of these experiments were conducted with morphine or codeine, it is reasonable to generalize the results to all mu opioid receptor agonists. In mice and rats, caffeine or other methylxanthines potentiated morphine-induced analgesia in several tests of nociception (Malec & Michalska, 1988; 1990; Misra et al., 1985). This appears to be mediated via modulation of the descending inhibitory opioid system rather than an effect on the spinal opioid system (DeLander & Hopkins, 1986). In clinical trials, caffeine at doses of 26.5 mg or less does not potentiate or may antagonize opioid analgesia. However, at doses greater than 50 mg, caffeine slightly potentiates opioid analgesia (Beaver, 1984; Zhang, 2001). In most of these trials, caffeine appears to add about 10–15% to the analgesic effect of the opioid. In addition to enhanced analgesia, another major advantage of combining caffeine with narcotic analgesics is the counteraction of the sedative effect of opioids.

The pharmaceutical combinations of the present invention comprise an opioid or a non-opioid analgesic in an intimate admixture with an analgesic from the SCP series along with caffeine and a pharmaceutically acceptable carrier prepared according to conventional pharmaceutical techniques. Pharmaceutically acceptable carriers include solid or liquid fillers, diluents, and encapsulating substances. The amount of the carrier employed in conjunction with the combination is sufficient to provide a practical quantity of material per unit dose of analgesic.

Pharmaceutically acceptable carriers for oral administration include, sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Pharmaceutically acceptable carriers for parenteral administration include isotonic saline, propylene glycol, ethyl oleate, pyrrolidone, aqueous ethanol, sesame oil, corn oil, and combinations thereof.

Various oral dosages forms can be employed, including solid forms such as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, and reconstituted solutions and/or suspensions.

Pharmaceutically effective combinations can typically contain between about 0.1 and about 1000 mg of an analgesic from the SCP series and between about 50 and about 200 mg of caffeine. The preferred pharmaceutically effective combinations contain between about 400 and about 1000 mg of an analgesic from the SCP series and between about 50 and about 150 mg of caffeine. Higher doses of caffeine, up to about 1000 mg, may be employed if tolerated by the patient. The pharmaceutically effective amounts of the opioid and non-opioid analgesics in combination with analgesics in the SCP series are similar to the corresponding combinations of opioid and non-opioid analgesics with acetaminophen. The precise amounts of selected opioid and non-opioid analgesics for use in the present SCP/opioid or non-opioid analgesic/caffeine compositions will vary depending on the specific analgesic chosen, the weight and kind of mammal and the condition for which the drug is administered. Generally, the selected opioid or non-opioid analgesic can be employed in any amount known to be a pharmaceutically effective amount. When so combined, the pharmaceutical compositions unexpectedly results in the synergistic addition of analgesic activity of the SCP series and the opioid and/or non-opioid analgesic, a greater synergistic analgesic response of the SCP/opioid analgesic and SCP/non-opioid analgesic combinations due to the presence of caffeine, and a hastening of the onset of the analgesic response due to the presence of caffeine. More surprisingly, these results occur without antipyretic activity, without suppressing blood coagulation, and without the toxicity associated with conventional non-narcotic analgesics.

It is apparent from the instant specification that various modifications and changes may be made by those skilled in the art. It is therefore intended that the following claims be interpreted as covering all modifications and changes that fall within the true spirit and scope of the invention.

What is claimed is:

1. An analgesic composition comprising synergistic, safe, and pharmaceutically effective amounts of:
   (a) an opioid analgesic;
   (b) a non-narcotic analgesic of the general formula,

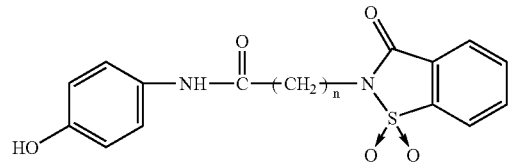

wherein n is a number from 1 to 5;
   (c) caffeine; and
   (d) a pharmaceutically acceptable carrier.

2. A composition according to claim 1, wherein the opioid analgesic is a phenanthrene alkaloid of opium.

3. A composition according to claim 1, wherein the opioid analgesic is selected from the group consisting of morphine and codeine.

4. A composition according to claim 1, wherein the opioid analgesic is selected from the group consisting of hydrocodone, oxycodone, hydromorphone, oxymorphone, metopon, apomorphine, normorphine, and N-(2-phenylethyl)-normorphine.

5. A composition according to claim 1, wherein the opioid analgesic is selected from the group consisting of etorphine and buprenorphine.

6. A composition according to claim 1, wherein the opioid analgesic is selected from the group consisting of dextromethorphan, butorphanol, levorphanol, levallorphan, cyclorphan, and racemorphan.

7. A composition according to claim 1, wherein the opioid analgesic is selected from the group consisting of phenazocine, pentazocine, and cylcazocine.

8. A composition according to claim 1, wherein the opioid analgesic is selected from the group consisting of meperidine, anileridine, piminodine, ethoheptazine, alphaprodine, betaprodine, diphenoxylate, loperamide, fentanil, sufentanil, alfentanil, and remifentanil.

9. A composition according to claim 1, wherein the opioid analgesic is selected from the group consisting of methadone, isomethadone, and propoxyphene.

10. An analgesic composition comprising synergistic, safe, and pharmaceutically effective amounts of:
    (a) a non-opioid analgesic;
    (b) a non-narcotic analgesic of the general formula,

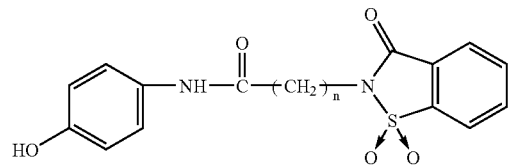

wherein n is a number from 1 to 5;
    (c) caffeine; and
    (d) a pharmaceutically acceptable carrier.

11. A composition according to claim 10, wherein the non-opioid analgesic is an NMDA receptor antagonist.

12. A composition according to claim 10, wherein the non-opioid analgesic is selected from the group consisting of dextromethorphan and ketamine.

13. A composition according to claim 10, wherein the non-opioid analgesic is an alpha$_2$ adrenoreceptor agonist.

14. A composition according to claim 10, wherein the non-opioid analgesic is selected from the group consisting of clonidine, metomidine, detomidine, dexmetomidine, dexmedetomidine and xylazine.

15. A composition according to claim 10, wherein the non-opioid analgesic is a monoamine re-uptake inhibitor.

16. A composition according to claim 10, wherein the non-opioid analgesic is tramadol.

17. A composition according to claim 10, wherein the non-opioid analgesic is a mixed agonist-antagonist analgesic.

18. A composition according to claim 10, wherein the non-opioid analgesic is selected from the group consisting of buprenorphine, dezocine and nalbuphine.

19. A method of alleviating pain in a mammal which comprises administering to said mammal affected with pain an effective amount of the composition of claim 1.

20. A method of alleviating pain in a mammal which comprises administering to said mammal affected with pain an effective amount of the composition of claim 2.

21. A method of alleviating pain in a mammal which comprises administering to said mammal affected with pain an effective amount of the composition of claim 3.

22. A method of alleviating pain in a mammal which comprises administering to said mammal affected with pain an effective amount of the composition of claim 4.

23. A method of alleviating pain in a mammal which comprises administering to said mammal affected with pain an effective amount of the composition of claim 5.

24. A method of alleviating pain in a mammal which comprises administering to said mammal affected with pain an effective amount of the composition of claim 6.

25. A method of alleviating pain in a mammal which comprises administering to said mammal affected with pain an effective amount of the composition of claim 7.

26. A method of alleviating pain in a mammal which comprises administering to said mammal affected with pain an effective amount of the composition of claim 8.

27. A method of alleviating pain in a mammal which comprises administering to said mammal affected with pain an effective amount of the composition of claim 9.

28. A method of alleviating pain in a mammal which comprises administering to said mammal affected with pain an effective amount of the composition of claim 10.

29. A method of alleviating pain in a mammal which comprises administering to said mammal affected with pain an effective amount of the composition of claim 11.

30. A method of alleviating pain in a mammal which comprises administering to said mammal affected with pain an effective amount of the composition of claim 12.

31. A method of alleviating pain in a mammal which comprises administering to said mammal affected with pain an effective amount of the composition of claim 13.

32. A method of alleviating pain in a mammal which comprises administering to said mammal affected with pain an effective amount of the composition of claim 14.

33. A method of alleviating pain in a mammal which comprises administering to said mammal affected with pain an effective amount of the composition of claim 15.

34. A method of alleviating pain in a mammal which comprises administering to said mammal affected with pain an effective amount of the composition of claim 16.

35. A method of alleviating pain in a mammal which comprises administering to said mammal affected with pain an effective amount of the composition of claim 17.

36. A method of alleviating pain in a mammal which comprises administering to said mammal affected with pain an effective amount of the composition of claim 18.

* * * * *

UNITED STATES PATENT AND TRADEMARK OFFICE
CERTIFICATE OF CORRECTION

| | | |
|---|---|---|
| PATENT NO. | : 7,064,140 B2 | Page 1 of 1 |
| APPLICATION NO. | : 10/459911 | |
| DATED | : June 20, 2006 | |
| INVENTOR(S) | : Carlos Sunkel et al. | |

It is certified that error appears in the above-identified patent and that said Letters Patent is hereby corrected as shown below:

In the Specification

At Column 1, Line number 17, change:
"Not applicable"

To:
--This invention was made with government support under EPS0092001 awarded by the National Science Foundation. The government has certain rights in the invention.--

Signed and Sealed this
Eighteenth Day of November, 2025

John A. Squires
*Director of the United States Patent and Trademark Office*